United States Patent [19]
Breitenbach et al.

[11] Patent Number: 5,753,770
[45] Date of Patent: May 19, 1998

[54] PREPARATION OF HYDROGEN PEROXIDE, C1 TO C4-MONOPERCARBOXYLIC ACID AND C4- TO C18-DIPERCARBOXYLIC ACID COMPLEXES IN A FLUIDIZED-BED PROCESS

[75] Inventors: Jörg Breitenbach, Linz; Sven Grabowski, Ludwigshafen; Axel Sanner, Frankenthal, all of Germany

[73] Assignee: BASF Aktiengesellschaft, Ludwigshafen, Germany

[21] Appl. No.: 663,321

[22] PCT Filed: Dec. 10, 1994

[86] PCT No.: PCT/EP94/04115

§ 371 Date: Jun. 21, 1996

§ 102(e) Date: Jun. 21, 1996

[87] PCT Pub. No.: WO95/17345

PCT Pub. Date: Jun. 29, 1995

[30] Foreign Application Priority Data

Dec. 23, 1993 [DE] Germany .................. 43 44 131.9

[51] Int. Cl.$^6$ ............... C08F 32/00; C08F 26/10; C08F 8/00; C08L 5/00
[52] U.S. Cl. ..................... 525/326.1; 525/326.7; 525/326.8; 525/326.9; 525/327.4; 525/327.5; 525/327.6; 525/328.4; 525/328.5; 525/329.4; 525/329.7; 525/387; 524/58
[58] Field of Search ............... 525/326.1, 326.7, 525/326.8, 326.9, 327.4, 327.5, 327.6, 328.4, 328.5, 329.4, 329.7, 387; 524/58

[56] References Cited

U.S. PATENT DOCUMENTS

| | | | |
|---|---|---|---|
| 3,376,110 | 4/1968 | Shiraeff et al. | 423/272 |
| 3,480,557 | 11/1969 | Shiraeff et al. | 252/186.29 |
| 3,494,907 | 2/1970 | Merijen et al. | 525/387 |
| 5,008,106 | 4/1991 | Merianos et al. | 525/387 |
| 5,066,488 | 11/1991 | Merianos et al. | 525/387 |
| 5,077,047 | 12/1991 | Biss et al. | 525/387 |
| 5,190,749 | 3/1993 | Login et al. | 514/772.5 |
| 5,238,978 | 8/1993 | Stein | 525/387 |

FOREIGN PATENT DOCUMENTS

92/02287  10/1992  WIPO.

*Primary Examiner*—Peter A. Szekely
*Attorney, Agent, or Firm*—Keil & Weinkauf

[57] ABSTRACT

A fluidized-bed process for preparing hydrogen peroxide, $C_1$–$C_4$-monopercarboxylic acids and $C_4$–$C_{18}$-dipercarboxylic acid complexes in which a solution of hydrogen peroxide, a $C_1$–$C_4$-monopercarboxylic acid, a $C_4$–$C_{18}$-dipercarboxylic acid or a mixture thereof in water or carboxylic acids is applied to a pulverulent or pregranulated matrix and fluidized-bed drying takes place.

8 Claims, No Drawings

PREPARATION OF HYDROGEN PEROXIDE, C1 TO C4-MONOPERCARBOXYLIC ACID AND C4- TO C18-DIPERCARBOXYLIC ACID COMPLEXES IN A FLUIDIZED-BED PROCESS

The present invention relates to an improved process for preparing hydrogen peroxide, $C_1$- to $C_4$-monopercarboxylic acid and $C_4$- to $C_{18}$-dipercarboxylic acid complexes in a fluidized-bed process by applying a solution of hydrogen peroxide, $C_1$- to $C_4$-monopercarboxylic acids, $C_4$- to $C_{18}$-dipercarboxylic acids or a mixture thereof in water or carboxylic acids to a pulverulent or pregranulated matrix in or outside the fluidized bed and simultaneous or subsequent fluidized-bed drying.

Since some of the complexes prepared by the process of the invention are new, the invention further relates to these novel substances.

U.S. Pat. No. 3,376,110 (1) and U.S. Pat. No. 3,480,557 (2) discloses water-insoluble (crosslinked) or water-soluble (uncrosslinked) hydrogen peroxide complexes of polymeric N-vinylheterocycles such as poly-N-vinylpyrrolidone and also poly-N-vinyl-2-caprolactam. These complexes can be prepared by evaporation of an aqueous suspension of polymer and hydrogen peroxide.

U.S. Pat. No. 5,077,047 (3) describes a process for preparing free-flowing pulverulent hydrogen peroxide/poly-N-vinylpyrrolidone complexes in a fluidized-bed process. The drying of the product formed can be carried out in the fluidized bed simultaneously or in a downstream step.

U.S. Pat. No. 5,190,749 (4) discloses that the fluidized-bed process from (3) can also be used for preparing hydrogen peroxide complexes from copolymers of N-vinylpyrrolidone with quaternized ammonium monomers.

Hydrogen peroxide/urea complexes can also be prepared in a fluidized-bed process according to DE-A 34 44 552 (5), with the drying of the reaction product being able to be carried out in one process step in the same apparatus or in a downstream drying step.

WO 92/17158 (7) discloses that a hydroxyalkylcellulose such as hydroxyethylcellulose can be added as foam pore enlarger to the hydrogen peroxide/poly-N-vinylpyrrolidone complexes during their preparation in a fluidized bed.

It is an object of the present invention to provide an improved preparation process for such hydrogen peroxide complexes, since the preparation processes described in the prior art are still not sufficiently efficient and economical. Furthermore, the known hydrogen peroxide/polymer complexes are deficient with regard to their properties during preparation and during use, so that there is also a need for new improved complexes of per-compounds.

We have found that this object is achieved by the process defined in the introduction for preparing hydrogen peroxide, $C_1$- to $C_4$-monopercarboxylic acid and $C_4$- to $C_{18}$-dipercarboxylic acid complexes in a fluidized-bed process, wherein the matrix used is A) an N-vinylcaprolactam homopolymer, B) an N-vinylcaprolactam copolymer with N-vinylpyrrolidone, N-vinylimidazole, acryl- or methacrylamidopropyl-3-sulfonic acid, acrylic or methacrylic acid or a mixture thereof as comonomer in a weight ratio of N-vinylcaprolactam to comonomer of from 20:1 to 1:20, C) an N-vinylpyrrolidone copolymer with N-vinylimidazole, acrylic or methacrylic acid or a mixture thereof as comonomer in a weight ratio of N-vinylpyrrolidone to comonomer of from 20:1 to 1:20, D) an N-vinylimidazole homopolymer which can be substituted on the heterocyclic ring by up to three $C_1$- to $C_4$-alkyl radicals and can be N-quaternized by $C_1$- to $C_4$-alkyl, E) a mixture of monosaccharides, oligosaccharides, polysaccharides or derivatives thereof with the polymers A to D in a weight ratio of from 1:99 to 90:10, F) a mixture of monosaccharides, oligosaccharides, starches, starch degradation products or derivatives thereof with N-vinylpyrrolidone homopolymers in a weight ratio of from 1:99 to 90:10, G) a mixture of trehalose, saccharose, glucose, α-, β- or γ-cyclodextrins or derivatives of these cyclodextrins or a mixture thereof with the polymers A to D or with N-vinylpyrrolidone homopolymers in a weight ratio of from 1:99 to 100:0 or H) in the case of $C_1$- to $C_4$-monopercarboxylic acid and $C_4$- to $C_{18}$-dipercarboxylic acid complexes, N-vinylpyrrolidone homopolymers.

For the purposes of the present invention, N-vinylcaprolactam is N-vinyl-ε-caprolactam (N-vinyl-2-caprolactam), and N-vinylpyrrolidone is N-vinyl-2-pyrrolidone.

Preferred copolymers B based on N-vinylcaprolactam are N-vinylcaprolactam/N-vinylpyrrolidone bipolymers, N-vinylcaprolactam/N-vinylimidazole bipolymers, N-vinylcaprolactam/N-vinylpyrrolidone/N-vinylimidazole terpolymers, N-vinylcaprolactam/acrylic or methacrylic acid bipolymers and N-vinylcaprolactam/acryl- or methacrylamidopropyl-3-sulfonic acid bipolymers. Any carboxylic acid or sulfonic acid groups present can be partially or completely present as salts, e.g. as sodium, potassium, ammonium or substituted ammonium salts.

Furthermore, the polymers B and also the homopolymers A can be uncrosslinked or crosslinked. The degree of water solubility can be adjusted by crosslinking. The process of the invention can be carried out particularly well using crosslinked N-vinylcaprolactam/N-vinylpyrrolidone copolymers ("Popcorn" polymers) as described in DE-C 24 37 629 (6). Crosslinking is best carried out by adding divinylethylene urea as crosslinking monomer in amounts of from 0.5 to 10% by weight, preferably from 2 to 8% by weight, based on the weight of the monomers specified under B, during the polymerization. However, it is also possible to effect crosslinking by addition of catalysts such as alkali metal hydrides or borohydrides.

In the copolymers B, the weight ratio of N-vinylcaprolactam to the comonomers N-vinylpyrrolidone, N-vinylimidazole, acryl- or methacrylamidopropyl-3-sulfonic acid and/or acrylic or methacrylic acid is from 20:1 to 1:20, preferably from 15:1 to 1:4, in particular from 10:1 to 1:1.

Preferred copolymers C based on N-vinylpyrrolidone are N-vinylpyrrolidone/N-vinylimidazole bipolymers and N-vinylpyrrolidone/acrylic acid or methacrylic acid bipolymers. The copolymers C can be uncrosslinked or crosslinked in a manner similar to the polymers A and B.

In the copolymers C, the weight ratio of N-vinylpyrrolidone to the comonomers N-vinylimidazole and/or acrylic or methacrylic acid is from 20:1 to 1:20, preferably from 4:1 to 1:10, in particular from 1:1 to 1:8.

Suitable N-vinylimidazole homopolymers D substituted by up to three, preferably by up to two, particularly preferably by one, $C_1$- to $C_4$-alkyl radical are, for example, those of 2-methyl-, 4-methyl- or 5-methylimidazole.

Suitable N-vinyl-N'-$C_1$- to $C_4$-alkylimidazolium homopolymers D are, for example, N-vinyl-N'-methyl-, N-vinyl-N'-ethyl- or N-vinyl-N'-butylimidazolium homopolymers. Counterions to the cationic quaternary nitrogen atoms can be, for example, chloride, bromide or methosulfate. The quaternization of the nitrogen atoms can have been carried out prior to or after the polymerization. The homopolymers D can be uncrosslinked or crosslinked in a manner similar to the polymers A to C.

The mixtures E and F of the polymers A to D or N-vinylpyrrolidone homopolymers with carbohydrates or carbohydrate derivatives show particularly good use properties, in particular, the dissolution properties of the final hydrogen peroxide or percarboxylic acid complexes are optimum. The weight ratio of the carbohydrates or carbohydrate derivatives to the specified polymers is from 1:99 to 90:10, preferably from 10:90 to 70:30, in particular from 20:80 to 50:50.

The carbohydrate component is a natural product based on monosaccharides, oligosaccharides, polysaccharides or their derivatives. From an economic point of view, the preparation preferably uses starches, thermally and/or mechanically treated starches, oxidatively, hydrolytically or enzymatically degraded starches, oxidized hydrolytically degraded starches or oxidized enzymatically degraded starches, or chemically modified starches or chemically modified monosaccharides or oligosaccharides. In principle, all starches are suitable. The starches are virtually insoluble in water and can be converted into a water-soluble form in a known manner by thermal and/or mechanical treatment or by enzymatic or acid-catalyzed degradation.

Examples which may be mentioned of starch degradation products which are obtainable either by oxidative, hydrolytic or enzymatic degradation of starch are the following compounds: dextrins such as white and yellow dextrins, maltodextrins, glucose syrup, maltose syrup, hydrolysates having a high content of D-glucose or maltose and D-glucose or their isomerization product fructose.

Other saccharides which are suitable as component B are monosaccharides and oligosaccharides such as galactose, mannose, ribose, saccharose, raffinose, lactose, trehalose and degradation products of cellulose, for example cellubiose and their oligomers. The cyclodextrins of various ring size and their derivatives are also suitable.

Preference is given to unreduced saccharides.

If, as described under G, the carbohydrate component used is trehalose, saccharose, glucose, α-, β- or γ-cyclodextrins or derivatives of these cyclodextrins or mixtures thereof, their proportion in the matrix material can be increased to 100% by weight, ie. the per-compound can even be applied to the pure carbohydrate in the process of the invention. The weight ratio of these carbohydrate components to the polymers A to D or N-vinylpyrrolidone homopolymers can thus be, going beyond E or F, from 1:99 to 100:0, preferably from 10:90 to 100:0, in particular from 20:80 to 100:0.

The Fikentscher K values as a measure of the molecular weight of the polymers A to D and H used are mostly from 10 to 90, in particular from 17 to 60, measured under the customary conditions therefor, eg. in $H_2O$ at room temperature.

In the preparation of the polymers A to D and H or of the polymers forming the basis of the mixtures E to G, it is possible to add small amounts of further customary copolymerizable monomers to slightly modify the properties of these polymers for the purposes of the present invention.

Suitable $C_1$- to $C_4$-monopercarboxylic acids (monoperoxycarboxylic acids) are primarily $C_2$- to $C_4$-monopercarboxylic acids, in particular peracetic acid, perpropionic acid, perbutyric acid and isoperbutyric acid. Performic acid can also be used if the necessary safety precautions are taken, bearing in mind the instability of this compound.

Suitable $C_4$- to $C_{18}$-dipercarboxylic acids (diperoxycarboxylic acids) are primarily $C_8$- to $C_{14}$-dipercarboxylic acids, in particular 1,12-diperoxydodecanoic acid and 1,14-diperoxytetradecanoic acid.

Use is made of solutions of the per-compounds having a per-compound content of normally from 1 to 80% by weight, in particular from 3 to 50% by weight, in the case of hydrogen peroxide or of from 0.5 to 30% by weight, in particular from 1 to 15% by weight, in the case of the percarboxylic acids, in water, in carboxylic acids, usually the carboxylic acids on which the per-compound is based, or mixtures of water and carboxylic acids. When using percarboxylic acids, aqueous solutions usually contain additional hydrogen peroxide.

The application of the aqueous solutions of the per-compounds to the pulverulent or pregranulated matrix A to H is preferably carried out in a fluidized bed, but it can also be carried out in an upstream step. The application is advantageously carried out by spraying of the solutions by means of nozzles.

The fluidized-bed drying to remove the water introduced mainly by the aqueous solutions of the per-compounds is preferably carried out simultaneously with the application of the per-compounds to the matrix, but can also be carried out in a separate step in the same or in a downstream apparatus. To obtain a free-flowing, ie. pourable, powder of the hydrogen peroxide or percarboxylic acid complexes, the water content should be less than 5% by weight after drying; this avoids blocking.

The temperature during application of the aqueous solutions of the per-compounds is usually from 25° to 80° C. for the inlet air and from 25° to 70° C. for the outlet air; for both inlet and outlet air, preference is given to a temperature range of from 30° to 60° C. in each case, in particular from 35° to 55° C. Further details for carrying out such a fluidized-bed process with regard to theoretical fundamentals, reactor types and industrial embodiments can be found in Ullmanns Encyklopädie der technischen Chemie, 4th edition, volume 3 (1973), pp. 433–460 and pp. 480–493.

The hydrogen peroxide and percarboxylic acid complexes prepared by the process of the invention have per-compound contents of from 1 to 35% by weight, preferably from 3 to 30% by weight, in particular from 5 to 25% by weight, based on the solids content in the product obtained.

The hydrogen peroxide and percarboxylic acid complexes described can, in principle, also be obtained without problems and with the same yields, purities and per-compound contents by precipitation from aqueous solutions of the polymers A to D and H by addition of aqueous solutions of the per-compounds, filtering or decanting off and drying, but this method cannot be satisfactorily transferred to a large scale.

The present invention also provides a hydrogen peroxide, $C_1$- to $C_4$-monopercarboxylic acid or $C_4$- to $C_{18}$-dipercarboxylic acid complex of an N-vinylcaprolactam copolymer with N-vinylpyrrolidone, N-vinylimidazole, acryl- or methacrylamidopropyl-3-sulfonic acid, acrylic or methacrylic acid or a mixture thereof as comonomer in a weight ratio of N-vinylcaprolactam to comonomer of from 20:1 to 1:20, containing from 1 to 35% by weight of per-compounds.

The present invention further provides a hydrogen peroxide, $C_1$- to $C_4$-monopercarboxylic acid or $C_4$- to $C_{18}$-dipercarboxylic acid complex of a N-vinylpyrrolidone copolymer with N-vinylimidazole, acrylic or methacrylic acid or a mixture thereof as comonomer in a weight ratio of N-vinylpyrrolidone to comonomer of from 20:1 to 1:20, containing from 1 to 35% by weight of per-compounds.

The present invention further provides a hydrogen peroxide, $C_1$- to $C_4$-monopercarboxylic acid or $C_4$- to $C_{18}$-dipercarboxylic acid complex of an N-vinylimidazole homopolymer which can be substituted on the heterocyclic ring by up to three $C_1$- to $C_4$-alkyl radicals and can be N-quaternized by $C_1$- to $C_4$-alkyl, containing from 1 to 35% by weight of per-compounds.

The present invention further provides a hydrogen peroxide, $C_1$- to $C_4$-monopercarboxylic acid or $C_4$- to $C_{18}$-dipercarboxylic acid complex of a mixture of monosaccharides, oligosaccharides, polysaccharides or derivatives thereof with (a) an N-vinylcaprolactam homopolymer, (b) an N-vinylcaprolactam copolymer with N-vinylpyrrolidone, N-vinylimidazole, acryl- or methacrylamidopropyl-3-sulfonic acid, acrylic or methacrylic acid or a mixture thereof as comonomer in a weight ratio of N-vinylcaprolactam to comonomer of from 20:1 to 1:20, (c) an N-vinylpyrrolidone copolymer with N-vinylimidazole, acrylic or methacrylic acid or a mixture thereof as comonomer in a weight ratio of N-vinylpyrrolidone to comonomer of from 20:1 to 1:20 or (d) an N-vinylimidazole homopolymer which can be substituted on the heterocyclic ring by up to three $C_1$- to $C_4$-alkyl radicals and can be N-quaternized by $C_1$- to $C_4$-alkyl, in a weight ratio of from 1:99 to 90:10, containing from 1 to 35% by weight of per-compounds.

The present invention further provides a hydrogen peroxide, $C_1$- to $C_4$-monopercarboxylic acid or $C_4$- to $C_{18}$-dipercarboxylic acid complex of a mixture of monosaccharides, oligosaccharides, starches, starch degradation products or derivatives thereof with an N-vinylpyrrolidone homopolymer in a weight ratio of from 1:99 to 90:10, containing from 1 to 35% by weight of per-compounds.

The present invention further provides a hydrogen peroxide, $C_1$- to $C_4$-monopercarboxylic acid or $C_4$- to $C_{18}$-dipercarboxylic acid complex of a mixture of trehalose, saccharose, glucose, α-, β- or γ-cyclodextrins or mixtures of these cyclodextrins or a mixture thereof with (a) an N-vinylcaprolactam homopolymer, (b) an N-vinylcaprolactam copolymer with N-vinylpyrrolidone, N-vinylimidazole, acryl- or methacrylamidopropyl-3-sulfonic acid, acrylic or methacrylic acid or a mixture thereof as comonomer in a weight ratio of N-vinylcaprolactam to comonomer of from 20:1 to 1:20, (c) an N-vinylpyrrolidone copolymer with N-vinylimidazole, acrylic or methacrylic acid or a mixture thereof as comonomer in a weight ratio of N-vinylpyrrolidone to comonomer of from 20:1 to 1:20, (d) an N-vinylimidazole homopolymer which can be substituted on the heterocyclic ring by up to three $C_1$- to $C_4$-alkyl radicals and can be N-quaternized by $C_1$- to $C_4$-alkyl, or (e) an N-vinylpyrrolidone homopolymer in a weight ratio of from 1:99 to 100:0, containing from 1 to 35% by weight of per-compounds.

The present invention further provides a $C_1$- to $C_4$-monopercarboxylic acid or $C_4$- to $C_{18}$-dipercarboxylic acid complex of an N-vinylpyrrolidone homopolymer, containing from 1 to 35% by weight of per-compounds.

Using the process of the invention it is possible to obtain hydrogen peroxide and percarboxylic acid complexes of various hydrophilicity as a function of the proportion of hydrophobic comonomer such as N-vinylcaprolactam in an efficient and economical manner. Particularly in the case of matrix material based on N-vinylcaprolactam, the fluidized-bed drying proceeds more quickly than in the case of N-vinylpyrrolidone homopolymers, since the former is less hygroscopic; such powders are free flowing. In warm storage of the complexes of per-compounds prepared by means of the matrix materials A to H, the products prepared according to the invention generally achieve better results in stability testing (for example by means of differential thermogravimetry) than the products of the prior art.

Differential thermogravimetry (heating rate of 2° K/min, 30°–400° C.) gives an onset temperature of 110° C. and a peak maximum temperature of 165° C. for an uncrosslinked polyvinylcaprolactam/$H_2O_2$ complex containing 4.8% by weight of $H_2O_2$. In contrast, a commercial uncrosslinked polyvinylpyrrolidone/$H_2O_2$ complex containing 18% by weight of $H_2O_2$ has an onset temperature of only 60° C. and a peak maximum temperature of 155° C.

Hydrogen peroxide and percarboxylic acid complexes prepared by the process of the invention can be used, for example, as a disinfectant or preservative, in particular in toothpastes, in treatment of acne, as wound dressings, in cosmetics, eg. in hair cosmetics (hair coloring, hair bleaching) and in depilation, or as solid components for chemical reactions such as polymerizations or oxidations, furthermore as detergent additive or as auxiliary in bleaching of textiles and paper, and also as constituents of filter systems, eg. for water treatment or in medicine for blood treatment, into which the complexes described with crosslinked polymers can be incorporated or to which they can be applied.

EXAMPLES

In testing as disinfectant according to the guidelines of the Deutsche Gesellschaft fur Hygiene und Mikrobiologie (DGHM), the minimum inhibition concentration was determined. In this test, a commercial uncrosslinked polyvinylpyrrolidone/$H_2O_2$ complex (20.2% by weight of $H_2O_2$) gave a value of 5.0%, while an uncrosslinked polyvinylcaprolactam/$H_2O_2$ complex (10.9% by weight of $H_2O_2$) gave a value of 5.0% and an $H_2O_2$ complex with a mixture of an uncrosslinked polyvinylpyrrolidone and maltodextrin (as described in Example 4 or 5 below) containing 10.1% by weight of $H_2O_2$ gave a value of 2.5%.

Testing was here carried out in accordance with the Richtlinien für die Prüfung und Bewertung chemischer Desinfektionsverfahren (version: Jan. 1, 1981) of the DGHM. Evaluation is carried out after incubation for 72 hours at 36° C. Dilution is carried out using water of standardized hardness without further auxiliaries (surfactants). The adjustment of the pH to 7.2 is carried out using 0.1 mol/l NaOH or using 0.1 mol/l HCl. The test concentration steps were in accordance with the following dilution steps (all values in % by volume):

100, 75, 50, 25, 20, 15, 10, 7.5, 5.0, 4.0, 3.0, 2.5, 2.0, 1.5, 1.00, 0.75, 0.50, 0.25, 0.10, 0.05, 0.025, 0.0125, 0.00625

(and so forth in a geometric series, ie. the concentration reduced by a factor of 0.5 each time).

Preparation in a fluidized-bed process

Fluidized-bed granulation was carried out in a granulation cylinder which was bounded at the bottom by a perforated plate with attached sieve (mesh size 10–500 μm) and at the top by 4 filter sacks which were blown clean every 15 seconds by compressed air. A two-fluid nozzle having an extended liquid inlet was located 28 cm above the sieve plate. The metering in of the hydrogen peroxide or peracetic acid solution was carried out by means of a peristaltic pump. The process air was also able to be replaced by nitrogen. The air throughput was about 120 m$^3$/h and was able to be roughly regulated by means of an outlet air flap. During drying, the air flow was increased to 150 m$^3$/h. The possible input amount of solid polymer powder for this apparatus was from 100 to 4000 g. The mean particle size was able to be adjusted by means of the two parameters feed rate and air pressure of the spray nozzle.

Example 1

150 g of N-vinylcaprolactam homopolymer were initially charged in the fluidized bed and sprayed at about 50° C. with a 30% strength by weight hydrogen peroxide solution. At intervals in the portion-wise addition of the hydrogen peroxide solution, the powder was completely dried in the air stream. Further drying could be carried out after the process was complete, but was not absolutely necessary.

Table 1 shows the amount of $H_2O_2$ solution applied and the $H_2O_2$ content found in the solid product:

TABLE 1

| $H_2O_2$ solution [g] | $H_2O_2$ content [% by weight] |
|---|---|
| 10 | 1.2 |
| 20 | 2.82 |
| 30 | 4.34 |
| 40 | 5.71 |
| 50 | 6.68 |
| 60 | 5.1 |
| 70 | 8.72 |
| 80 | 9.98 |
| 90 | 9.63 |
| 100 | 10.9 |

Example 2

N-vinylpyrrolidone/N-vinylimidazole "Popcorn" polymer (weight ratio 1:8) was initially charged as powder (154 g), sprayed at an inlet air temperature of 50° C. with a 30% strength by weight hydrogen peroxide solution and dried in a similar manner to Example 1.

Table 2 shows the amount of $H_2O_2$ solution applied and the $H_2O_2$ content found in the solid product:

TABLE 2

| $H_2O_2$ solution [g] | $H_2O_2$ content [% by weight] |
|---|---|
| 10 | 2.75 |
| 20 | 5.59 |
| 30 | 8.22 |
| 40 | 10.4 |
| 50 | 13.2 |
| 60 | 15.4 |
| 70 | 17.1 |

TABLE 2-continued

| $H_2O_2$ solution [g] | $H_2O_2$ content [% by weight] |
|---|---|
| 80 | 18.7 |
| 90 | 19.5 |
| 100 | 20.5 |

Example 3

Normally polymerized N-vinylpyrrolidone/N-vinylimidazole copolymer (weight ratio 1:8) was likewise used as powder and reacted under the same conditions as in Example 1. The final content of hydrogen peroxide was 19.5% by weight.

Example 4

75 g of N-vinylpyrrolidone homopolymer and 25 g of maltodextrin were initially charged as matrix material. The experimental conditions were as in Example 1.

Table 3 shows the amount of $H_2O_2$ solution applied and the $H_2O_2$ content found in the solid product:

TABLE 3

| $H_2O_2$ solution [g] | $H_2O_2$ content [% by weight] |
|---|---|
| 10 | 2.51 |
| 20 | 5.55 |
| 30 | 7.72 |
| 40 | 8.84 |
| 50 | 10.6 |

Example 5

65 g of N-vinylpyrrolidone homopolymer and 35 g of maltodextrin were initially charged as matrix material. The experimental conditions were as in Example 1.

Table 4 shows the amount of $H_2O_2$ solution applied and the $H_2O_2$ content found in the solid product:

TABLE 4

| $H_2O_2$ solution [g] | $H_2O_2$ content [% by weight] |
|---|---|
| 10 | 1.46 |
| 20 | 4.28 |
| 30 | 8.83 |
| 40 | 10.8 |
| 50 | 11.4 |

Example 6

N-vinylpyrrolidone/N-vinylcaprolactam copolymer having a weight ratio of 1:9 was initially charged (100 g). The experimental conditions were as in Example 1.

Table 5 shows the amount of $H_2O_2$ solution applied and the $H_2O_2$ content found in the solid product:

TABLE 5

| $H_2O_2$ solution [g] | $H_2O_2$ content [% by weight] |
|---|---|
| 10 | 2.7 |
| 20 | 5.8 |
| 30 | 8.4 |
| 40 | 11.2 |

TABLE 5-continued

| $H_2O_2$ solution [g] | $H_2O_2$ content [% by weight] |
|---|---|
| 50 | 13.3 |
| 60 | 15.7 |
| 70 | 16.7 |
| 80 | 18.4 |
| 90 | 19.4 |
| 100 | 21.7 |

Example 7

Use of an N-vinylpyrrolidone/N-vinylcaprolactam/N-vinylimidazole terpolymer having a weight ratio of 5:1:2 (100 g) and addition of 100 g of $H_2O_2$ enabled a final content of 20.3% by weight of $H_2O_2$ to be achieved.

Example 8

Use of a cross-linked N-vinylcaprolactam/N-vinylpyrrolidone copolymer having a weight ratio of 1:1 (100 g) enabled a final content of 32% by weight of $H_2O_2$ to be achieved.

Example 9

100 g of N-vinylpyrrolidone homopolymer (K value: 30, measured in $H_2O$ at 25° C.) were treated with 5% strength by weight aqueous peracetic acid solution containing 26–27% by weight of hydrogen peroxide, at an inlet air temperature of 40° C. and an outlet air temperature of 35° C., and dried in a similar manner to Example 1.

Table 6 shows the amount of peracid solution applied and the $H_2O_2$/peracid contents found in the solid product:

TABLE 6

| Peracid solution [g] | $H_2O_2$/peracid content [% by weight] |
|---|---|
| 10 | 1.7/0.7 |
| 20 | 4.0/1.2 |
| 30 | 6.7/1.5 |
| 40 | 7.7/1.7 |

After 4 hours at 70° C., the complex lost about 10% of the hydrogen peroxide content and 12% of the peracetic acid content.

Example 10

An N-vinylpyrrolidone/N-vinylcaprolactam copolymer having a weight ratio of 1:9 (100 g) was treated in a similar manner to Example 9.

Table 7 shows the amount of peracid solution applied and the $H_2O_2$/peracid contents found in the solid product:

TABLE 7

| Peracid solution [g] | $H_2O_2$/Peracid content [% by weight] |
|---|---|
| 10 | 1.9/0.5 |
| 20 | 4.2/0.9 |
| 30 | 6.9/1.5 |
| 40 | 8.5/1.9 |

Example 11

100 g of crosslinked N-vinylpyrrolidone homopolymer were treated in a similar manner to Example 9.

Table 8 shows the amount of peracid solution applied and the $H_2O_2$/peracid contents found in the solid product:

TABLE 8

| Peracid solution [g] | $H_2O_2$/Peracid content [% by weight] |
|---|---|
| 10 | 1.8/0.4 |
| 20 | 4.1/0.8 |
| 30 | 6.9/1.4 |
| 40 | 7.9/1.8 |

After 7 hours at 70° C., the complex lost about 11% of the hydrogen peroxide content and 10% of the peracetic acid content.

We claim:

1. A process for preparing hydrogen peroxide, $C_1$- to $C_4$-monopercarboxylic acid and $C_4$- to $C_{18}$-dipercarboxylic acid complexes in a fluidized-bed process which comprises: applying a solution of hydrogen peroxide, $C_1$- to $C_4$-monopercarboxylic acids, $C_4$- to $C_{18}$-dipercarboxylic acids or a mixture thereof in water or carboxylic acids to a pulverulent or pregranulated matrix in or outside the fluidized bed and simultaneous or subsequent fluidized-bed drying, wherein the matrix used is A) an N-vinylcaprolactam homopolymer,
   B) an N-vinylcaprolactam copolymer with N-vinylpyrrolidone, N-vinylimidazole, acryl- or methacrylamido-propyl-3-sulfonic acid, acrylic or methacrylic acid or a mixture thereof as comonomer in a weight ratio of N-vinylcaprolactam to comonomer of from 20:1 to 1:20,
   C) an N-vinylpyrrolidone copolymer with N-vinylimidazole, acrylic or methacrylic acid or a mixture thereof as comonomer in a weight ratio of N-vinylpyrrolidone to comonomer of from 20:1 to 1:20,
   D) an N-vinylimidazole homopolymer which can be substituted on the heterocyclic ring by up to three $C_1$- to $C_4$-alkyl radicals and can be N-quaternized by $C_1$- to $C_4$-alkyl radicals,
   E) a mixture of monosaccharides, oligosaccharides or polysaccharides with one or more of the polymers A to D in a weight ratio of from 1:99 to 90:10,
   F) a mixture of monosaccharides, oligosaccharides, starches or starch degradation products with N-vinylpyrrolidone homopolymers in a weight ratio of from 1:99 to 90:10,
   G) a mixture of trehalose, saccharose, glucose, α-, β-, or γ-cyclodextrins or a mixture thereof with one or more of the polymers A to D or with N-vinylpyrrolidone homopolymers in a weight ratio of from 1:99 to 100:0 or
   H) in the case of $C_1$- to $C_4$-monopercarboxylic acid and $C_4$- to $C_{18}$-dipercarboxylic acid complexes, N-vinylpyrrolidone homopolymers.

2. A hydrogen peroxide, $C_1$- to $C_4$-monopercarboxylic acid or $C_4$- to $C_{18}$-dipercarboxylic acid complex of an N-vinylcaprolactam copolymer with N-vinylpyrrolidone, N-vinylimidazole, acryl- or methacrylamidopropyl-3-sulfonic acid, acrylic or methacrylic acid or a mixture thereof as comonomer in a weight ratio of N-vinylcaprolactam to comonomer of from 20:1 to 1:20, containing from 1 to 35% by weight of per-compounds.

3. A hydrogen peroxide, $C_1$- to $C_4$-monopercarboxylic acid or $C_4$- to $C_{18}$-dipercarboxylic acid complex of an N-vinylpyrrolidone copolymer with N-vinylimidazole, acrylic or methacrylic acid or a mixture thereof as comonomer in a weight ratio of N-vinylpyrrolidone to comonomer of from 20:1 to 1:20, containing from 1 to 35% by weight of per-compounds.

4. A $C_1$- to $C_4$-monopercarboxylic acid or $C_4$- to $C_{18}$-dipercarboxylic acid complex of an N-vinylimidazole homopolymer which can be substituted on the heterocyclic ring by up to three $C_1$- to $C_4$-alkyl radicals and can be N-quaternized by $C_1$- to $C_4$-alkyl radicals, containing from 1 to 35% by weight of per-compounds.

5. A hydrogen peroxide, $C_1$- to $C_4$-monopercarboxylic acid or $C_4$- to $C_{18}$-dipercarboxylic acid complex of a mixture of monosaccharides, oligosaccharides or polysaccharides with (a) an N-vinylcaprolactam homopolymer, (b) an N-vinylcaprolactam copolymer with N-vinylpyrrolidone, N-vinylimidazole, acryl or methacrylamidopropyl-3-sulfonic acid, acrylic or methacrylic acid or a mixture thereof as comonomer in a weight ratio of N-vinylcaprolactam to comonomer of from 20:1 to 1:20, (c) an N-vinylpyrrolidone copolymer with N-vinylimidazole, acrylic or methacrylic acid or a mixture thereof as comonomer in a weight ratio of N-vinylpyrrolidone to comonomer of from 20:1 to 1:20 or (d) an N-vinylimidazole homopolymer which can be substituted on the heterocyclic ring by up to three $C_1$- to $C_4$-alkyl radicals and can be N-quaternized by $C_1$- to $C_4$-alkyl radicals, in a weight ratio of from 1:99 to 90:10, containing from 1 to 35% by weight of per-compounds.

6. A hydrogen peroxide, $C_1$- to $C_4$-monopercarboxylic acid or $C_4$- to $C_{18}$-dipercarboxylic acid complex of a mixture of monosaccharides, oligosaccharides, starches or starch degradation products with an N-vinylpyrrolidone homopolymer in a weight ratio of from 1:99 to 90:10, containing from 1 to 35% by weight of per-compounds.

7. A hydrogen peroxide, $C_1$- to $C_4$-monopercarboxylic acid or $C_4$- to $C_{18}$-dipercarboxylic acid complex of a mixture of trehalose, saccharose, glucose, $\alpha$-, $\beta$- or $\gamma$-cyclodextrins or a mixture thereof with (a) an N-vinylcaprolactam homopolymer, (b) an N-vinylcaprolactam copolymer with N-vinylpyrrolidone, N-vinylimidazole, acryl- or methacrylamidopropyl-3-sulfonic acid, acrylic or methacrylic acid or a mixture thereof as comonomer in a weight ratio of N-vinylcaprolactam to comonomer of from 20:1 to 1:20, (c) an N-vinylpyrrolidone copolymer with N-vinylimidazole, acrylic or methacrylic acid or a mixture thereof as comonomer in a weight ratio of N-vinylpyrrolidone to comonomer of from 20:1 to 1:20, (d) an N-vinylimidazole homopolymer which can be substituted on the heterocyclic ring by up to three $C_1$- to $C_4$-alkyl radicals and can be N-quaternized by $C_1$- to $C_4$-alkyl radicals, or (e) an N-vinylpyrrolidone homopolymer in a weight ratio of from 1:99 to 100:0, containing from 1 to 35% by weight of per-compounds.

8. A $C_1$- to $C_4$-monopercarboxylic acid or $C_4$- to $C_{18}$-dipercarboxylic acid complex of an N-vinylpyrrolidone homopolymer, containing from 1 to 35% by weight of per-compounds.

* * * * *